United States Patent
Rapaport et al.

(12) 
(10) Patent No.: US 6,335,436 B1
(45) Date of Patent: *Jan. 1, 2002

(54) OLIGONUCLEOTIDES ACTIVE AGAINST DRUG-RESISTANT BACTERIA

(75) Inventors: Eliezer Rapaport, Belmont; Valeri Metelev; Paul C. Zamecnik, both of Shrewsbury, all of MA (US)

(73) Assignee: Hybridon, Inc., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 1 days.

(21) Appl. No.: 08/976,970

(22) Filed: Nov. 24, 1997

Related U.S. Application Data

(63) Continuation of application No. 08/387,423, filed on Feb. 10, 1995, now abandoned.

(51) Int. Cl.$^7$ ............... C07H 21/04; C12N 1/21; C12N 15/00; C12N 15/11
(52) U.S. Cl. ............ 536/24.5; 536/23.1; 536/25.32; 435/252.1; 435/253.1; 435/440; 435/471
(58) Field of Search ............ 435/6, 69.1, 91.1, 435/172.3, 243, 252.1, 253.1, 320.1, 375, 440, 471; 536/23.7, 23.1, 24.32, 24.5; 514/44

(56) References Cited

U.S. PATENT DOCUMENTS

| | | |
|---|---|---|
| 4,671,958 A | 6/1987 | Rodwell et al. |
| 4,806,463 A | 2/1989 | Goodchild et al. |
| 5,108,921 A | 4/1992 | Low et al. |
| 5,138,045 A | 8/1992 | Cook et al. |
| 5,166,320 A | 11/1992 | Wu et al. |
| 5,218,105 A | 6/1993 | Cook et al. |
| 5,276,019 A | 1/1994 | Cohen et al. |
| 5,294,533 A * | 3/1994 | Lupski et al. |
| 5,338,837 A | 8/1994 | Kahne |
| 5,354,844 A | 10/1994 | Beug et al. |
| 5,391,723 A | 2/1995 | Priest |
| 5,686,590 A | 11/1997 | Jacobs, Jr. et al. |
| 5,716,594 A * | 2/1998 | Elmaleh et al. |

FOREIGN PATENT DOCUMENTS

| | | |
|---|---|---|
| CH | 676247 A5 | 12/1990 |
| EP | 0 305 145 | 3/1989 |
| WO | WO 89/07615 | 8/1989 |
| WO | PCT/US90/01002 | 2/1990 |
| WO | PCT/US91/02224 | 3/1991 |
| WO | PCT/US90/05272 | 4/1991 |
| WO | PCT/US92/07339 | 9/1992 |
| WO | PCT/US92/05085 | 12/1992 |
| WO | 9313740 * | 7/1993 |
| WO | PCT/US93/12246 | 12/1993 |
| WO | 9402498 * | 2/1994 |
| WO | WO 94/26765 | 11/1994 |

OTHER PUBLICATIONS

Branch. TIBS. 23, 45–50 (Feb. 1998).*
Gewirtz et al. PNAS. 93. 3161–3163 (Apr. 1996).*
Gasparro et al. Antisense Res and Development 1:117–140 (1991).*
Rahman et al. Antisense Res and Development 1:319–327 (1991).*
Chrisey et al. Antisense Res and Development 3:367–381 (1993).*
Rastogi et al. Antimicrobial Agents and Chemotherapy 34, 759–764 (May 1990).*
Hoffner et al. Acta Leprologica 7 (Suppl. 1): 195–199 (1989).*
Partridge et al. FEBS Letters 288, 30–32 (Aug. 1991).*
Milligan et al., J. Med. Chem. 36(14):1923–1936, 1993.*
Uhlmann, Chem. Rev., 90:544–584, 1990.*
Rajanasakul, Adv. Drug. Del. Rev., 18:115–131, 1996.*
Gura, Science 270:575–577, 1995.*
Rojanasakul, Adv. Drug. Del. Rev., 18:115–131, 1996.*
Iseman, M.D., The New England J. Med., Sep. 9, 1993 vol. 329 (11) pp. 784–791.*
Kilburn et al, Antimicrobial Agents and Chemotherapy vol. 19. (2) pp. 346–348, 1981.*
Temsamani et al, J. Biol. Chem., vol. 266 (1) pp. 468–472 1991.*
Erichsen, C., et al., "Effect of N–Phosphonacetyl–L–aspartate and D–Glucosamine on the Incorporation of 5–Fluorouridine into Normal Tissue and an Adenocarcinoma in the Rat". Anticancer Res., 7:77–80 (1987).
Rosner, A., et al., "Evaluation of Several Enrichment Procedures for the Isolation of Recombinant Plasmid DNA". Molec. Biol. Rep. 4(4):253–256 (1978).
Hotta, K., et al. "PCR Inhibition Assay for DNA–targeted Antibiotics". Journal of Antibiotics, 48(11): 1267–1272 (1995).
Matsuda, Y., et al., "Some Evidence for Interaction of D–Cycloserine with DNA". J. of Antibiotics, 35(7): 893–899 (1982).
Rapaport, E., et al., "Antimycobacterial activities of antisense oligodeoxynucleotide phosphorothioates in drug–resistant strains". Proc. Natl. Acad. Sci. USA 93:709–713 (1996).
Berkow, R., et al., "The Merck Manual of Diagnosis and Therapy". Merck & Co., Rahway, 113–120 (1987).
Beltinger, et al., Binding, Uptake, and Intracellular Trafficking of Phosphorothioate–modified Oligodeoxynucleotides, J. Clin. Invest, 95:1814–1823 (1995).

(List continued on next page.)

Primary Examiner—Sean McGarry
Assistant Examiner—Mark L. Shibuya
(74) Attorney, Agent, or Firm—Hale and Dorr LLP

(57) ABSTRACT

The invention discloses methods and materials for the utilization of chemically modified oligonucleotides in the treatment of drug-resistant bacterial infections including drug-resistant tuberculosis.

26 Claims, No Drawings

OTHER PUBLICATIONS

Editorial, Reviving the Antibiotic Miracle? Science 264:360–365 (1994).

Alland, et al., Transmission of Tuberculosis in New York City, An analysis by DNA Fingerprinting and conventional epidemiologic methods, New Engl J. Med. 330:1710–1716 (1994).

Small, et al., The Epidemiology of Tuberculosis in San Francisco. A population based study using conventional and molecular methods, New Engl J. Med. 330:1703–1709 (1994).

Editorial, The Global Challenge of Tuberculosis. The Lancet 334:277–279 (1994).

Iseman. Treatment of Multi Drug–Resistant Tuberculosis. New Engl J. Med 329:784–791 (1993).

Temsamani, et al. Biotinylated Antisense Methylphosphonate Oligodeoxynucleotides J. Biol. Chem. 266: 468–472, 1991.

Sande, et al. Chemotheraphy of Microbial Diseases, In:the Pharmacological Basis of Therapeutics, Gilman et al. Eds, Pergamon Press, 1990, pp. 1018–1046.

Cassan, et al., Nucleotide Sequence of IysC Gene Encoding the Lysine–Sensitive Aspartokinase III of *Escherichia coli*, K12, J. Biol. Chem. 261:1052–1057, 1986.

Zamecnik, et al., Inhibition of Rous Sarcoma Virus Replication and Cell Tranformation by a Specific Oligodeoxynucleotide: Proc. Natl. Acad. Sci. 75:280–284, 1978.

Stephenson et al., Inhibition of Rous Sarcoma Viral RNA Translation by a Specific Oligodeoxyribo–nucleotide: Proc. Nat. Acad. Sci. 75:285–288, 1978.

Zamecnik et al., Inhibition of Replication and Expression of Human T–cell Lymphotropic Virus Type III in Cultured Cells by Exogenous Synthetic Oligonucleotides Complementary to Viral RNA; Proc. Nat. Acad. Sci. 83:4143–4146, 1986.

Matsukura et al., Phosphorothioate Analogs of Oligodeoxynucleotides: Inhibitors of Replication and Cytopathic Effects of Human Immunodeficiency Virus; Proc. Nat. Acad. Sci.; 84:7706–7710, 1987.

Agrawal et al., Oligodeoxynucleoside Phosphoramidates and Phosphorothioates as Inhibitors of Human Immunodeficiency Virus; Proc.Nat.Acad.Sci., 85:7079–7083, 1988.

Sarin et al., Inhibition of Acquired Immunodeficiency Syndrome Virus by Oligodeoxynucleoside Methyl–phosphonates; Proc. Nat. Acad. Sci., 85:7448–7451, 1988.

Sartorius et al., Hybridization arrest of the cell–free translation of the malarial dihydrofolate reductase/thymidylate synthase mRNA by anti–sense oligodeoxyribonucleotides; Nucl.Acids Res. 19:1613–1618, 1991.

Agrawal, Antisense Oligonucleotides: A possible Approach for Chemotherapy of AIDS In: Prospects for Antisense Nucleic Acids Therapy of Cancer and AIDS, Wickstrom, Ed. Wiley–Liss, Inc. pp. 143–158, 1990.

Mandell et al., Antimacrobial Agents, Drugs used in the Chemotherapy of Tuberculosis and Leprosy, In: Pharmacalogical Basis of Therapeutics, Gilman, et al., Eds, Pergamon Press, 1146–1164 (1990).

Heym, et al., Implications of Multi Drug Resistance for the Future of Short–Course Chemotherapy of Lancet 344:293–298 (1994).

Jacobs, et al., Genetic Systems for Mycobacteria Meth. Enzymol. 204:537–555 (1991).

Rastogi, et al., Enhancement of Drug Susceptibility of Mycobacterium Avium by Inhibitors of Cell Envelope Synthesis, Antimicrob. Agents Chemother, 34:759–764 (1990).

Heifets, et al., Ethambutol MICs and MBCs for Mycobacterium Avium Complex and Mycobacterium Tuberculosis, Antimicrob. Agents Chemother. 30:927–932 (1986).

Hoffener, Studies on the Mechanism of Synergistic Effects of Ethambutol and Other Antibacterial Drugs on Mycobacterium Avium Complex. ACTA Leprologica (Geneva) 7 (Supplement 1):195–199 (1989).

Takayama, et al., Inhibition by Ethambutol of Mycolic Acid Transfer into the Cell Wall of Mycobacterium Smegmatis, Antimicrob. Agents Chemother, 16:240–242 (1979).

Silve, et al., Ethambutol Inhibition of Glucose Metabolism in Microbacteria: A Possible Target of the Drug. Antimicrobe. Agents Chemother, 37:1536–1538 (1993).

Heym, et al., Isolation and Characterization of Isoniazid–Resistant Mutants of Mycobacterium Smegmatis and M. Aurum. Res Microbial. 143:721–730 (1992).

Cardulo, et al., Detection of Nucleic Acid Hybridization by Non–Radioactive Fluorescents Resonance in Energy Tranfer Proc. Nat. Acad. Sci. USA 85:8790–8794 (1988).

Agrawal, et al., Efficient Synthesis of Oligoribonucleotide and its Phosphorothioate Analogue Using H–Phosphonate Approach. Tetrahedron Lett. 31:7541–7544 (1990).

Metelev, et al., Ion Exchange High–Performance Liquid Chromotography Analysis of Oligoribonucleotide Phosphorothioates. Anal. Biochem. 200:342–346 (1992).

Cirillo, et al., Isolation and Characterization of the Aspartokinase and Aspartate Semialdehyde Dehydrogenase Operon from Mycobacteria Mol. Microbiol. 11:629–639 (1994).

Chen et al., A novel gene delivery using EGF receptor–mediated endocytosis: FEBS Lett, 338:167–169 (1994).

Press Release: Proceedings of the National Academy of Sciences, Jan. 23, 1996.

Rapaport et al., Antimycobacterial Activities of Antisense Oligodeoxynucleotide Phosphorothioates in Drug–resistant Strains, Proc. Natl. Acad. Sci. USA.93:709–713 (1996).

Michael et al., Binding–incompetent Adenovirus Facilitates Molecular Conjugatemediated Gene Transfer by the Receptor–mediated Endocytosis Pathway. The J. Biol. Chem. 268(10):6886–6889 (1993).

Takayama et al., Inhibition of Synthesis of Arabinogalactan by Ethambutol in Mycobacterium Smegmatis. Antimicrobial Agents and Chemotherapy. 33(9):1493–1499 (1989).

* cited by examiner

OLIGONUCLEOTIDES ACTIVE AGAINST DRUG-RESISTANT BACTERIA

This application is a continuation of application Ser. No. 08/387,432, filed Feb. 10, 1995, now abandoned.

FIELD OF THE INVENTION

The present invention discloses the treatment of bacterial infections through the use of chemotherapeutic agent, antisense oligonucleotides. The invention also discloses the treatment of infections caused by bacteria such as *Mycobacterium tuberculosis* having resistance to one or more conventional chemotherapeutic agents.

BACKGROUND OF THE INVENTION

The emergence of drug-resistant bacteria in general and drug-resistant tuberculosis in particular is rapidly becoming a major public health problem in the U.S. and miracle? Science 264: 360–365, 1994). The urgency in finding new treatment modalities for drug-resistant tuberculosis is emphasized by two recently published molecular and conventional epidemiological studies (Alland, D., et al. Transmission of tuberculosis in New York City. An analysis by DNA fingerprinting and conventional epidemiologic methods. New Engl. J. Med. 330: 1710–1716, 1994; Small, P. M., et al. The epidemiology of tuberculosis in San Francisco. A population-based study using conventional and molecular methods. New Engl. J. Med., 330: 1703–1709, 1994). Not only was it demonstrated by utilization of DNA fingerprinting that more than a third of the newly diagnosed TB cases in New York and San Francisco are the result of recent person to person transmission, rather than activation of latent infections, but also that nearly half of the isolates from patients with recently transmitted infections in New York were drug-resistant *M. tuberculosis*. Of these drug-resistant isolates, half were resistant to multiple drugs. Drug-resistant *M. tuberculosis* strains, because of their ability to lead to a long infectious state, are especially active in the recent person to person transmissions.

Tuberculosis is the most widespread of human pathogenic diseases, having an annual number of new cases of active infection of 7.5 million cases and an annual number of deaths attributable to tuberculosis of 2.5 million worldwide according to the World Health Organization (Editorial, The Global Challenge of tuberculosis. The Lancet 344: 277–279, 1994).

Modern chemotherapy of tuberculosis began in 1952 with the development of isoniazid (isonicotinic acid hydrazide) which along with rifampin (or rifampicin) is still the mainstay of the treatment of tuberculosis. Streptomycin, which was shown to be effective in the treatment of tuberculosis before 1952, frequently resulted in treatment failure due to the rapidly developing resistance to streptomycin. Combinations of streptomycin with aminosalicylic acid and isoniazid were then utilized resulting in a high degree of cures in tuberculosis patients. The antituberculosis drugs that currently are being clinically utilized are isoniazid, rifampin, pyrazinamide and ethambutol as first line oral drugs; streptomycin, amikacin, kanamycin and capreomycin as injectable drugs; ofloxacin, ciprofloxacin, ethionamide, aminosalicylic acid and D-cycloserine as second-line oral drugs (Iseman, M. D. Treatment of multidrug-resistant tuberculosis. New England Journal of Medicine 329: 784–791, 1993; Mandell, G. L. and Sande, M. A. Antimicrobial agents, drugs used in the chemotherapy of tuberculosis and leprosy in The Pharmacological Basis of Therapeutics, Gilman A.G. et al. Editors, Pergamon Press, 1990, pp. 1146–1164).

Drug resistance and multidrug resistance in tuberculosis originates in spontaneous mutations which occur at predictable rates in the tubercle bacilli. The mutations are not linked and the rise of drug-resistant organisms is the result of these pre-existing mutations rather than a result of drug treatment or another novel mechanism not yet established or understood (Heym, B. et al. Implications of multidrug resistance for the future of short-course chemotherapy of tuberculosis: a molecular study. The Lancet 344: 293–298, 1994). Thus, the emergence of drug resistance is the direct result of the survival of random pre-existing mutations and the selection of the mutation-carrying organisms due to the killing of drug-sensitive organisms by effective drugs. Drug resistance in tubercle bacilli does not involve mechanisms related to the existence of increased efflux of drugs through multidrug resistant (MDR) channels as is the case with parasites such as *Plasmodium falciparum*.

Oligonucleotides containing a base sequence complementary to selected sequences present on mRNAs were shown during the last several years to inhibit the synthesis of the specific proteins coded for by the targeted mRNAs. These oligonucleotides, known as antisense comprise a new class of therapeutic agents and have been demonstrated to inhibit the replication and expression of human immunodeficiency virus (HIV), as well as other viruses or cellular proteins in in vitro or in vivo screening systems. The internucleoside phosphate group of oligodeoxynucleotides can be chemically modified, for example, to methylphosphonates, phosphorothioatea, or phosphoroamidates in order to increase nuclease resistance of the modified oligonucleotide, without serious effects on its base sequence-specific hybridization to target mRNAs. Such modifications can afford reductions in the 50% inhibitory concentrations ($IC_{50}$) to the $10^{-7}$ M range.

U.S. Pat. No. 4,806,463 entitled "Inhibition of HTLV-III by exogenous oligonucleotides" to Goodchild and Zamecnik disclosed for the first time the use of modified oligonucleotides including oligodeoxynucleotide phosphorothioates which are oligonucleotides modified on the internal phosphate groups, for inhibiting the replication and gene expression of HTLV-III virus now called Human Immunodeficiency Virus (HIV). U.S. Pat. No. 5,276,019 entitled "Inhibitors for replication of retroviruses and for the expression of oncogene products" to Cohen et al. also discloses the use of modified oligodeoxynucleotide phosphorothioates for inhibiting viral replication in a host as well as inhibiting the replication of a human immunodeficiency virus replication in particular. The disclosures of these two patents are incorporated herein by reference.

Oligonucleotide drugs inhibit the expression of specific genes by three potential mechanisms. For RNA targets, at least two mechanisms of inhibition can be envisioned. Oligodeoxynucleotide hybridization to the complementary RNA sequences may inhibit the processing, nuclear export, or translation of mRNA by blocking the access of functional machinery to requisite mRNA sequences. Alternatively, oligodeoxynucleotide hybridization may lead to RNA cleavage by means of RNase H activities, which are DNA-RNA hybrid-dependent ribonucleases present in all cells examined. Evidence for both RNase H-dependent and independent modes of action has been presented for mRNA translational inhibition by complementary oligodeoxynucleotides in cell-free systems. Oligonucleotides can also be targeted to specific sequences of the DNA double helix where they inhibit transcription of specific genes (antigen or triplex strategy). The development of oligonucleotides and their modifications as therapeutic agents has been accelerated by recent advances in synthetic oligonucleotide chemistry.

SUMMARY OF THE INVENTION

Experimental evidence to establish that antisense technology can be extended to treating bacterial infections has not before existed to the knowledge of the inventors. If further has been unknown whether the mechanism of drug resistance in *Mycobacterium tuberculosis* would act to exclude oligonucleotides introduced exogenously. Finally, it was unknown whether antisense oligonucleotides would gain access through the bacterial cell wall if introduced exogenously, even for nonresistant strains.

The present invention discloses the use of antisense oligonucleotides for inhibiting bacterial growth and thus for the treatment of bacterial infections. Since bacterial infection previously was treated by a cheap, effective and readily available assortment of antibacterial agents, a significant aspect of the present invention is the disclosure that growth of bacteria resistant to one or more of the conventional therapeutic agents nonetheless can be readily inhibited by antisense oligonucleotides. The present invention demonstrates that conventional mechanisms which yield drug-resistant bacteria do not operate to exclude oligonucleotides and that antisense oligonucleotides can circumvent drug-resistance in bacteria.

According to one aspect of the invention, a method for treating an infection caused by a bacterium is provided. The method involves administering to a subject, preferably a human, in need of such treatment an effective amount of an antisense oligonucleotide that inhibits the growth of the bacterium. Useful oligonucleotides include oligoribonucleotides, oligodeoxyribonucleotides and modified versions of the same. Modified versions include those with modified internucleoside linkages such as phosphorothioate linkages, methylphosphonate linkages and phosphoroamidate linkages. Phosphorothioates are preferred. The oligonucleotides also may be chemically modified at either or both ends to prevent nucleolytic degradation. The oligonucleotides are constructed and arranged such that they hybridize under physiological conditions to a bacterial gene, the expression of which is essential for bacterial metabolism and growth. The invention is not limited to treatment of any particular bacterial infection, although preferred is treatment of infection by drug resistant strains of bacteria.

Various methods are provided for delivering the oligonucleotides of the invention in effective amounts. In one aspect of the invention, the subject is simultaneously treated with a compound such as ethambutol, which labilizes the bacterial wall and facilitates the delivery of the oligonucleotide into the bacterium. In another aspect of the invention, the oligonucleotides may be linked to a molecule that enhances bacterial wall transport. For example, the oligonucleotides may be covalently linked to a ligand for a receptor on a bacterium. Examples of ligands include D-cycloserine, D-glucosamine and biotin.

According to other aspects of the invention, articles of manufacture are contemplated. For example, antibacterial cocktails may be prepared which include a labilizing agent and the oligonucleotides of the invention. As another example, the invention provides an antibacterial agent that is an oligonucleotide of the invention covalently coupled to a molecule that enhances transport of the oligonucleotide across the bacterial cell wall. Such a molecule can be a ligand for a receptor on a bacterium. Specific examples include antisense oligonucleotides covalently coupled to D-cycloserine, D-glucosamine or biotin.

DETAILED DESCRIPTION OF THE INVENTION

The present invention discloses the development of a class of compounds, antisense oligonuleotides, which enter bacterial cells and by hybridizing in a sequence-specific manner to a target nucleic acid act in inhibiting the synthesis of specific proteins which are essential for survival and growth of the bacterial cell. The present invention further discloses the chemical modification of such antisense oligonucleotides.

Antisense oligonucleotides of the invention are short oligonucleotides (about 12–36 nucleotides long) which are comprised of a base sequence complementary to a bacterial nucleic acid sequence. Chemical modifications of oligonucleotides can be produced at their 5' or 3' ends, at the inter-nucleoside phosphate or any other synthetic inter-nucleoside moiety, at the sugar moiety or on the bases themselves. When applied exogenously, these oligomers may enter the target cell and by virtue of their sequence-specific hybridization to target mRNA sequences, inhibit the synthesis of targeted proteins.

In order to demonstrate the invention, we have utilized the bacterium *Mycobacterium smegmatis* which is very closely related to *M. tuberculosis* and which is predictive as to the clinical outcome after a drug is shown to be effective in an in vitro screening system. Justification for the use of *M. smegmatis* as a common and acceptable model for the development of a therapeutic modality against drug-resistant tuberculosis is due to the following well-acknowledged factors:

I. *M. smegmatis* shares significant genetic sequences with *M. tuberculosis*. The antisense drug developed relies on hybridization with the mycobacterial genetic machinery for the inhibition of expression of proteins essential for growth;

II. *M. smegmatis* has been utilized in the past as an initial mycobacterial model for the development of antituberculosis drugs because of its faster rate of proliferation as compared to *M. tuberculosis;*

III. *M. smegmatis*, which is a non-pathogen in man, is the preferred choice for studies of targeted drug development in drug-resistant *M. tuberculosis*. Utilization of multidrug-resistant (MDR) *M. tuberculosis* for these studies would be impossible because of the requirements for extensive microbiological and biochemical manipulations, which would produce an unacceptable risk and require a much longer period of initial studies. *Mycobacterium smegmatis* has been commonly used as a model for the biochemical studies and efficacy screening related to the development of antimycobacterial drugs in general and antituberculosis drugs in particular.

It has been discovered that under many conditions, oligodeoxynucleotide phosphorothioates do not enter bacteria. Two strategies were successfully utilized to enable entry of oligonucleotides into bacterial cells. One employed the presence of very low levels of ethambutol and the other involved utilization of oligomers covalently attached to a D-cycloserine molecule whereby entry into the bacterial cell is achieved by a receptor-mediated process. Significant sequence-specific growth inhibition of *Mycobacterium smegmatis* was obtained by modified oligonucleotides complementary in sequence to a specific region of the mycobacterium aspartokinase (ask) gene when utilized in combinations with ethambutol (as compared to ethambutol alone) or as a D-cycloserine covalent adduct without the presence of any other cytotoxic or cytostatic agent. Sequence-specific oligodeoxynucleotide phosphorothioate to which a molecule of D-glucosamine was covalently attached is taken up by *Mycobacterium smegmatis* in the presence of ethambutol at a much higher rate than the unmodified oligomer under the same conditions resulting in substantially increased growth inhibition and indicating an upregulation of hexose uptake due to the inhibition by ethambutol of the synthesis of carbohydrate precursors of cell wall.

We thus demonstrate here that modified oligonucleotides can be utilized for the inhibition of bacterial growth and that the growth of isoniazid-resistant, rifampicin-resistant and streptomycin-resistant strains of $M.$ smegmatis can be inhibited to the same degree as drug-sensitive strains of the same organism. The present invention therefore demonstrates that modified oligonucleotides can circumvent drug-resistance in bacteria.

We have conducted experiments utilizing Mycobacterium smegmatis grown in liquid medium (Jacobs, Jr., W. R., Kalpana, G. V., Cirillo, J. D., Pascopella, L., Snapper, S. B., Udani, R. A., Jones, W., Barletta, R. G. and Bloom, B. R. Genetic systems for mycobacteria. Methods in Enzymology. 204: 537–555, 1991), which show that these bacterial cells do not allow entry of oligodeoxynucleotide phosphorothioates across the bacterial cell membrane and into the intracellular compartments. Under normal condition no significant growth inhibitory activity was observed with a wide range of oligodeoxynucleotide phosphorothioates up to concentrations of 25 μM. The mycobacterial cell envelope architecture and especially the outer wall layer (OL) have been long known to prevent entry of hydrophilic drugs into the mycobacterial cell and to favor entry of lipophilic drugs which are easily solubilized within the lipid portion of the outer wall layer (Rastogi, N., Goh, K. S. and David, H. L. Enhancement of drug susceptibility of Mycobacterium avium by inhibitors of cell envelope synthesis. Antimicrob. Agents Chemother. 34: 759–764, 1990). Ethambutol, a drug which has been in clinical practice for the treatment of tuberculosis and infections caused by other mycobacteria since 1966 (Heifets, L. B., Iseman, M. D. and Lindholm-Levy, P. J. Ethambutol MICs and MBCs for Mycobacterium avium complex and Mycobacterium tuberculosis. Antimicrob. Agents Chemother. 30: 927–932, 1986 and references cited therein) was reported to be effective in increasing drug susceptibility of mycobacteria by inhibiting cell envelope synthesis (Hoffner, S. E., Källenius, G., Beezer, A. E. and Sevenson, S. B. Studies on the mechanisms of synergistic effects of ethambutol and other antibacterial drugs on Mycobacterium avium complex. Acta Leprologica (Geneva) 7 (Suppl 1): 195–199, 1989). The mechanisms of ethambutol activities in disrupting cell wall synthesis in mycobacteria have been identified. They include the inhibition of mycolic acid transfer into the cell wall (Takayama, K., Armstrong, E. L., Kunugi, K. A., and Kilburn, J. O. Inhibition by ethambutol of mycolic acid transfer into the cell wall of Mycobacterium smegmatis. Antimicrob. Agents Chemother. 16: 240–242, 1979) and the inhibition of biosynthesis from glucose of monosaccharides utilized for the synthesis of cell wall oligo- and polysaccharides (Takayama, K. and Kilburn, J. O. Inhibition of synthesis of arabinogalactan by ethambutol in Mycobacterium smegmatis. Antimicrob. Agents Chemother.33: 1493–1499, 1989). These initial effects of ethambutol are followed by the decrease of mycolic acid transfer into mycobacterial cell wall as being the final result of the ethambutol promoted inhibition of cell wall arabinogalactan accumulation (Silve, G., Valero-Guillen, P., Quemard, A., Dupont, M.-A., Daffe, M. and Laneelle, G. Ethambutol inhibition of glucose metabolism in mycobacteria: a possible target of the drug. Antimicrob. Agents Chemother. 37: 1536–1538, 1993). It was discovered in the present invention that ethambutol can promote the uptake by bacteria of antisense oligonucleotides.

Determination of growth of $M.$ smegmatis was performed in liquid cultures (Jacobs, Jr., W. R. et al. Genetic systems for mycobacteria, supra) with cell counting that was done by an electronic Coulter Counter Model ZM with an appropriate probe for counting bacterial particles. This method of cell counting is highly accurate as we have shown by its equivalency with plating on agar and colony counts after serial dilutions. The assessment of growth by colony growth in Middlebrook 7H10 agar was being utilized as well. Growth of $M.$ smegmatis was determined by actual cell counts as well as determinations of MIC (minimum inhibitory concentration) and MBC (minimum bacteriocidal concentration) which are the minimal concentrations of inhibitors required to inhibit growth of at least 99% of the bacterial cells (MIC) or to kill at least 99% of the bacterial population (MBC). Wild type strains of $M.$ smegmatis were either mc$^2$155 (kindly supplied by W. R. Jacobs, Jr.) (Jacobs Jr. W. R. et al. Genetic systems for mycobacteria, supra) and other single colony isolates from ATCC (Amer.Tissue Culture Collection) strain 607 isolated by ourselves. Strains resistant to isoniazid, rifampin or streptomycin were isolated in our laboratory according to published procedures that are based on the existence of spontaneous $M.$ smegmatis mutations which yield resistance to a single drug at mutational frequencies of $10^{-6}$ to $10^{-7}$ (Heym, B. and Cole, S. T. Isolation and characterization of isoniazid-resistant mutants of Mycobacterium smegmatis and $M$ aurum. Res. Microbiol. 143: 721–730, 1992). All the methodologies for the synthesis and modifications of oligodeoxynucleotides and their modifications follow published procedures (Cardullo, R. A., Agrawal, S. Flores, C., Zamecnik, P. C. and Wolf, D. E. Detection of nucleic acid hybridization by nonradiative fluorescence resonance energy transfer. Proc. Natl. Acad. Sci. USA 85: 8790–8794, 1988 Agrawal, S. and Tang, J. Y. Efficient synthesis of oligoribonucleotide and its phosphorothioate analogue using H-phosphonate approach. Tetrahedron Letters 31: 7541–7544, 1990; Metelev, V. and Agrawal, S. Ion exchange high-performance liquid chromatography analysis of oligonucleotide phosphorothioates. Anal. Biochem. 200: 342–346, 1992).

Utilizing ethambutol in liquid medium at levels of 0.5–1.0 μg/ml, which are 5–10-fold lower than the plagma levels that are achieved in man (Mandell, G. L. and Sande, M.A. Antimicrobial agents, in The Pharmacological Basis of Therapeutics. Gilman, A. G., Rall, T. W., Nies, A. S. and Taylor P., Editors, pp. 1152–1153, Pergamon Press, 1990), $M.$ smegmatis became susceptible to the entry and inhibition of growth, as compared to ethambutol treatment alone, by oligodeoxynucleotide phosphorothioates directed at specific genetic targets. Several different oligodeoxynucleotide phogphorothioates complementary to several sense sequences of the coding and non-coding regions of published mycobacterial gene nucleotide sequences were synthesized. Antisense oligomers complementary to a conserved region of mycobacterial aspartokinase gene (ask) were proven highly effective in inhibiting growth of $M.$ smegmatis in the liquid medium screening system (Table I). The aspartokinase (ask) gene, which was identified upstream of and in an operon with the aspartate semialdehyde dehydrogenase (asd) gene, codes for a protein that catalyzes key biosynthetic pathways (Cirillo, J. D., Weisbrod, T. R., Pascopella, L., Bloom, B. R. and Jacobs, Jr., W. R. Isolation and characterization of the aspartokinase and aspartate semialdehyde dehydrogenase operon from mycobacteria. Mol. Microbiol. 11: 629–639, 1994).

TABLE I

Inhibition of *M. smegmatis* Growth in Broth Cultures by Oligodeoxynucleotide Phosphorothioates (ODS) in the Presence of Ethambutol[a]

| Strain[b] | Ethambutol ug/ml | ODS at 2.5 µM Initial Concentration | Cell Numbers per ml x 10^6 | | |
|---|---|---|---|---|---|
| | | | 24 hrs | 48 hrs | 72 hrs |
| ATCC 607 | None | None | 620[c] | 605 | 582 |
| | None | ODS8[d] | 610 | 602 | 593 |
| | None | ODS33[e] | 612 | 603 | 590 |
| | None | ODS55[f] | 615 | 600 | 585 |
| | 0.5 | None | 71 | 240 | 411 |
| | 0.5 | ODS8 | 32 | 49 | 60 |
| | 0.5 | ODS33 | 33 | 48 | 57 |
| | 0.5 | ODS55 | 30 | 45 | 52 |
| | 1 | None | 39 | 109 | 172 |
| | 1 | ODS8 | 18 | 37 | 40 |
| | 1 | ODS33 | 15 | 20 | 33 |
| | 1 | ODS55 | 15 | 21 | 34 |
| | 5 | None | 25 | 68 | 111 |
| | 5 | ODS8 | 14 | 27 | 44 |
| | 5 | ODS33 | 14 | 21 | 37 |
| | 5 | ODS55 | 13 | 13 | 20 |

[a]Data represent the averages of two independent experiments.
[b]All inoculations were performed with 10 x 10^6 cells per ml of culture. Results for another wild type strain of *M. smegmatis* as well as for isoniazid-resistant, streptomycin-resistant and rifampicin-resistant strains of *M. smegmatis* were quantitatively similar.
[c]620 x 10^6 cells per ml represent the saturation density of *M. smegmatis* cells in liquid culture under these conditions.
[d]A 21-mer (21 nucleotides in length) oligodeoxynucleotide phosphorpthioate complementary to nucleotide sequence 1533-1553 of the *M. smegmatis* ask-asd operon.
[e]A 27-mer oligodeoxynucleotide phosphorothioate complementary to nucleotide sequence 1527–1553 of the *M. smegmatis* ask-asd operon.
[f]A 36-mer oligodeoxynucleotide phosphorothioate complementary to nucleotide sequence 1518–1553 of the *M. smegmatis* ask-asd operon.

The region of nucleotide sequence 1499–1553 inside the reading frame of *M. smegmatis* ask-asd operon which contains a single transcriptional start at the 5'-end of the ask gene was proven the best genetic target (Table I). This region codes for a highly conserved sequence among mycobacterial and other bacterial species and is indicated to code for the active site of the aspartokinase protein (Cirillo, J. D. et al. Isolation and characterization of the aspartokinase and aspartate semialdehyde dehydrogenase operon from mycobacteria. supra). The bacterial growth inhibition efficacy of antisense oligonucleotides with complementary sequences directed against this particular region of the ask gene is further understood in light of its expected additional inhibition of the asd gene expression. Both the Ask and Asd proteins catalyze biosynthetic reactions which affect the mycobacterial cell wall Integrity. Several 21-mer and 27-mer oligonucleotides complementary to various segments of this region demonstrated efficacy in combinations with ethambutol.

Assays of the sensitivity of oligodeoxynucleotide phosphorothioates in inhibiting growth of *M. smegmatis* were conducted in liquid medium in the presence of low levels of ethambutol (0.5–5.0 µg/ml) and effective oligomers yielded up to 90% inhibition of growth at 2.5 µM concentration as compared to growth in the presence of the same levels of ethambutol alone (Table II). Parent and *M. smegmatis* strains resistant to isoniazid, rifampicin and streptomycin selected in our lab from an ATCC 607 colony as a parent strain followed by isolation of the drug-resistant mutants according to published general procedures (Heym, B. and Cole, S. T. Isolation and characterization of isoniazid-resistant mutants of *Mycobacterium smegmatis* and *Mycobacterium aurum*. supra) yielded the same sensitivity to the antisense oligonucleotide-mediated growth inhibition thus indicating the circumvention of individual drug resistance.

TABLE II

MIC of Ethambutol in the presence of Oligodeoxynucleotide Phosphorothioates in Broth Cultures.[a]

| Strain[b] | ODS | Initial ODS Concentration µM | MIC[c] µg/ml |
|---|---|---|---|
| ATCC 607 | None | None | 25 |
| | ODS33[d] | 1 | 20 |
| | ODS33 | 2.5 | 10 |
| | ODS33 | 10 | 7.5 |
| mc^2 155 | None | None | 30 |
| | ODS33 | 1 | 20 |
| | ODS33 | 2.5 | 12.5 |
| | ODS33 | 10 | 7.5 |

[a]Data represent the average of two independent experiments.
[b]All inoculations were performed with 100 x 10^6 cells per ml of culture. Results were similar for the isoniazid-resistant, streptomycin-resistant and rifampicin-resistant strains.
[c]The MICs were determined as the minimum concentration of ethambutol that inhibited at least 99% of cell growth during two weeks in a broth culture.
[d]Described in the footnote to Table I.

Since ethambutol leads to intracellular depletion of cell wall monosaccharide precursors and the inhibition of growth of *M. smegmatis* by ethambutol can be reversed by additions of D-glucosamine, D-galactose, D-mannose or D-arabinose but not by the addition of D-glucose or D-fructose (Silve, G. et al. ethambutol inhibition of glucose metabolism in mycobacteria: a possible target of the drug. supra), we capitalized on a potential pregulation of cell wall monosaccharide precursor uptake by *M. smegmatis* in the presence of ethambutol. Oligonucleotides that were effective in inhibiting *M. smegmatis* growth in the presence of ethambutol were covalently attached to D-glucosamine via a phosphate linker at the oligonucleotide 3'-end utilizing established chemical procedures involving H-phogphonate chemistry with purification and analysis as referred to earlier. The covalent adduct of D-glucosamine to oligodeoxynucleotide phosphorothioates yields marked increases in the growth inhibitory activities of the oligonucleotides in the presence of ethambutol (Table III).

TABLE III

Inhibition of *M. smegmatis* Growth in Broth Cultures by Covalently-Modified Oligodeoxynucleotide Phosphorothioates[a]

| Strain[b] | Ethambutol µg/ml | ODS at 5 µM Initial Concentration | Cell Numbers per ml x 10^6 | | |
|---|---|---|---|---|---|
| | | | 24 hrs | 48 hrs | 72 hrs |
| ATCC 607 | None | None | 650 | 609 | 582 |
| | None | ODS8-DA[c] | 581 | 477 | 417 |
| | None | ODS8-DS[d] | 268 | 213 | 128 |
| | None | ODS8-LS[e] | 604 | 541 | 446 |
| | None | ODS8-DG[f] | 576 | 492 | 407 |
| | 0.5 | None | 77 | 189 | 388 |
| | 0.5 | ODS8-DA | 45 | 67 | 120 |
| | 0.5 | ODS8-DS | 52 | 63 | 105 |

TABLE III-continued

Inhibition of *M. smegmatis* Growth in Broth
Cultures by Covalently-Modified
Oligodeoxynucleotide Phosphorothioates[a]

| Strain[b] | Ethambutol µg/ml | ODS at 5 µM Initial Concentration | Cell Numbers per ml × 10⁶ | | |
|---|---|---|---|---|---|
| | | | 24 hrs | 48 hrs | 72 hrs |
| | 0.5 | ODS8-LS | 46 | 65 | 98 |
| | 0.5 | ODS8-DG | 31 | 26 | 44 |

[a]Data represent the average of two independent experiments.
[b]All inoculations were performed with 10 × 10⁶ cells per ml of culture. Results for another wild type strains of *M. smegmatis* as well as for isoniazid-resistant, streptomycin-resistant and rifampicin-resistant strains of *M. smegmatis* were quantitatively similar. 650 × 10⁶ cells per ml represent the saturation density of *M. smegmatis* in broth culture under these conditions.
[c]Oligonucleotide ODS8-DA is identical in its nucleotide sequence to ODS8 except for a covalent modification of its 3'-end with a molecule of D-alanine.
[d]Oligonucleotide ODS8-DS is identical in its nucleotide sequence to ODS8 except for a covalent modification at its 3'-end with a molecule of D-cycloserine.
[e]Oligonucleotide ODS8-LS is identical in its nucleotide sequence to ODS8 except for a covalent modification at its 3'-end with a molecule of L-cycloserine.
[f]Oligonucleotide ODS8-DG is identical in its nucleotide sequence to ODS8 except for a covalent modification at its 3'-end with a molecule of D-glucosamine.

After this initial success in utilizing a covalently attached ligand for the enhancement of uptake of an antisense oligonucleotide into *M. smegmatis*, we embarked on a search for a ligand that would enable the uptake and subsequent inhibition of growth of *M. smegmatis* by oligodeoxynucleotide phosphorothioates without the presence of ethambutol. The only ligand among the several that were synthesized and tested which yielded positive results was D-cycloserine. D-cycloserine is a broad spectrum antibiotic which has been utilized as part of an antituberculosis regimen (Mandell, G. L. and Sande, M. A. Antimicrobial agents, in The Pharmacological Basis of Therapeutics. Gilman, A. G., Rall, T. W., Nies, A. S. and Taylor, P. Editors, pp. 1156, Pergamon Press, 1990). It is generally thought to be taken up by the uptake system that is utilized for D-alanine since its inhibitory activities in bacteria are related to reactions in which D-alanine is involved in bacterial cell wall synthesis. Oligodeoxynucleotide phosphorothioates which inhibit *M. smegmatis* growth in the presence of ethambutol were covalently attached to D-cycloserine utilizing a 3'-end phosphate linker in a manner similar to the synthesis of D-glucosamine-modified oligomers. A 21-mer oligodeoxynucleotide phosphorothioate covalently attached to D-cycloserine and having a base sequence complementary to the previously discussed region of the ask gene typically yielded a 60–70% inhibition of *M. smegmatis* in liquid medium at a concentration of 5 µM (Table III). The same oligonucleotide without the D-cycloserine ligand or when covalently bound to L-cycloserine, D-or L-alanine, L-azaserine and a variety of other ligands, was without any effect on *M. smegmatis* growth under identical conditions (Table III). Free D-cycloserine itself, in liquid medium at levels equivalent to the levels present as a covalent part of the antisense oligonucleotide (1.0 µg/ml) yielded minimal inhibition of growth (Table IV). A 10–30 fold excess of this level of D-cycloserine, when present in the liquid medium (10–30 µg/ml), produced a significant inhibition of *M. smegmatis* growth. More importantly, these levels of free D-cycloserine, when present along with a 5 µM concentration of D-cycloserine-modified antisense oligonucleotides, did not add to the inhibitory activities of the modified oligonucleotide but actually reduced the level of inhibition to about the level achieved by free D-cycloserine (Table IV). These data indicate that free D-cycloserine is competing for the same receptor that is involved in the cellular uptake of the D-cycloserine-modified oligonucleotide and thus successfully blocks uptake and subsequent growth inhibitory activities of the D-cycloserine-modified oligonucleotide.

TABLE IV

Inhibition of *M. smegmatis* Growth in Broth
Cultures by Covalently-Modified
Oligodeoxynucleotide phosphorothioates[a]

| Strain[b] | ODS at 5 µM Initial Concentration | Free D-cycloserine µg/ml | Cell Numbers per ml × 10⁶ | | |
|---|---|---|---|---|---|
| | | | 24 hrs | 48 hrs | 72 hrs |
| ATCC 607 | None | None | 632 | 560 | 513 |
| | ODS8 | None | 610 | 557 | 495 |
| | ODS8-DS[c] | None | 291 | 233 | 168 |
| | ODS8-DS | 30 | 381 | 287 | 225 |
| | None | 1 | 617 | 549 | 504 |
| | None | 5 | 551 | 482 | 420 |
| | None | 30 | 363 | 291 | 236 |

[a]Data represent the average of two independent experiments.
[b]All inoculations were performed with 10 × 10⁶ cells per ml of culture. Results obtained with other wild type strains of *M. smegmatis* as well as with isoniazid-resistant, streptomycin-resistant and rifampicin-resistant strains of *M. smegmatis* were quantitatively similar. 632 × 10⁶ cells per ml represent the saturation density of *M. smegmatis* in broth culture under these conditions.
[c]As described in the footnote to Table III.

In conclusion, the present invention demonstrates through the use of drug-resistant *Mycobacterium smegmatis* as a scientifically acceptable model of drug-resistant tuberculosis in particular and drug-resistant bacteria in general that:

Oligodeoxynucleotides and their phosphorothioate derivatives (oligodeoxynucleotide phosphorothioates) with a nucleotide sequence complementary ("antisense") to sequences of genes that code for proteins that affect bacterial cell growth or metabolism, can be used for inhibiting bacterial growth in a fashion that circumvents resistance to a variety of drugs. The oligonucleotides, however, in many cases have to be afforded with facilitated entry across the bacterial cell membrane and into the bacterial cell, a process which is achieved by one of the following two methods:

I. The use of membrane labilizing agents such as ethambutol in mycobacteria which enables the entry of oligonucleotides into the mycobacterial cell with the resulting significant inhibition of bacterial cell growth.
 II. The use of oligonucleotides covalently attached to a small molecule which is a ligand of a bacterial cell receptor and thus enables the facilitated entry of the modified oligonucleotide into the bacterial cell without the presence of membrane labilizing agents. The rapid entry of these compounds into the bacterial cell is due to the interaction of the covalently bound ligand with its bacterial cell receptor. The covalently attached ligands do not affect the growth-inhibitory activities of the oligonucleotide inside the bacterial cell.

Chemical modifications of oligonucleotides protect these oligonucleotides from biological degradation by nuclease action and enable the covalent modification of the oligonucleotides with a small ligand molecule such as D-cycloserine or D-glucosamine as disclosed in this invention utilizing established chemical procedures involving H-phosphonate chemistry (Cardullo, R. A., Agrawal, S., Flores, C., Zamecnik, P. C. and Wolf, D. E. Detection of nucleic acid hybridization by nonradiative fluorescence resonance energy transfer. Proc. Natl. Acad. Sci. USA 85:8790–8794, 1988; Agrawal, S. and Tang, J. Y. Efficient synthesis of oligoribonucleotide and its phosphorothioate analogue using H-phosphonate approach. Tetrahedron Letters 31:7541–7544, 1990) with purification and analysis as described (Metelev, V. and Agrawal, S. Ion exchange high-performance liquid chromatography analysis of oligonucleotide phosphorothioates. Anal. Biochem. 200:342–346, 1992).

Another ligand which is actively taken up by a wide variety of bacterial cells and which is suitable for modification of oligodeoxynucleotides phosphorothioates in order to afford their facilitated entry into the bacterial cell is biotin. Techniques for biotinylation of oligonucleotides are well established (Temsamani, J., Agrawal, S. and Pederson, T. Biotinylated antisense methylphosphonate oligodeoxynucleotides. J. Biol. Chem. 266:468–472, 1991).

Although the examples above describe methods and products relating to *Mycobacterium smegmatis* and, by implication, *Mycobacterium tuberculosis*, the invention is not so limited. The invention is applicable to both resistant and nonresistant strains of bacteria in general.

Drug-resistance, as noted, is an emerging major public health problem and resistance to conventional effective, cheap antibiotics is evident in strains of a wide variety of microorganisms in addition to *Mycobacterium tuberculosis*. The invention thus has particular importance for treating such strains. Examples of bacterial strains which developed resistance to mainstay antibiotics include *Staphylococcus aureus, Streptococcus pneumoniae, Escherichia coli, Neisseria gonorrhoeae, Shigella flexneri, Haemophilus influenzae* and *Neisseria meningitidis* among disease causing bacteria (Sande, M. A., Kapusnik-Uner, J. E. and Mandell, G. L. Chemotherapy of Microbial Diseases, in the Pharmacological Basis of Therapeutics. Gilman, A. G., Rall, T. W., Nies, A. S. and Taylor, P., Editors, pp. 1018–1046, Pergamon Press, 1990). The methodology disclosed in the present invention can be utilized to inhibit the growth of a broad spectrum of bacterial species. As another specific example, in *E. coli* which actively takes up D-cycloserine (Mandell, G. L. and Sande, M. A. Antimicrobial agents, in the Pharmacological Basis of Therapeutics. Gilman, A. G, Rall, T. W., Nies, A. S. and Taylor, P., Editors, pp. 1156, Pergamon Press, 1990), the gene encoding aspartokinase III (Ask protein) has been sequenced (Cassan, M., Parsot, C., Cohen, G. N. and Patte, J.-C. Nucleotide sequence of lysC gene encoding the lysine-sensitive apartokinase III of *Escherichia coli* K12. J. Biol. Chem. 261:1052–1057, 1986) and therefore D.-cycloserine-modified oligodeoxynucleotide phosphorothioate with a base sequence complementary to the comparable region of *E. coli* ask gene is expected to inhibit the growth of the bacteria by mechanisms disclosed here.

Those skilled in the art will be able to determine, with no more than rqutine experimentation, genes that are essential for bacterial metabolism and growth and the regions of such genes that will be effective as antisense targets. Typically such regions are those that are highly conserved. Likewise, effective amounts for administration can be determined by no more than routine experimentation, and, of course, will depend upon the nature and severity of the condition and the size, age, physical condition and the like of the subject. An effective amount is that amount that will inhibit bacterial growth and/or metabolism in vivo. Typically, the highest dose tolerable without unacceptable side effects will be preferred. Various alternatives and equivalents will be apparent to those skilled in the art.

Having thus described our invention, what we claim as new and desire to secure by Letters Patent is:

1. An oligonucleotide covalently coupled to a ligand that binds to a receptor on a Mycobacterium; wherein the oligonucleotide hybridizes under physiological conditions to an aspartokinase gene, an aspartate semialdehyde dehydrogenase gene, or an aspartokinase-aspartate semialdehyde dehydrogenase operon of the Mycobacterium; and wherein the ligand is D-cycloserine, D-glucosamine or biotin.

2. The oligonucleotide of claim 1, wherein the Mycobacterium is *Mycobacterium smegmatis* or *Mycobacterium tuberculosis*.

3. The oligonucleotide of claim 1, wherein the oligonucleotide is an oligodeoxynucleotide or an oligoribonucleotide.

4. The oligonucleotide of claim 1, wherein the oligonucleotide is a modified oligonucleotide.

5. The oligonucleotide of claim 1, wherein the oligonucleotide is covalently modified at the 5' end, the 3' end, or the 5' end and the 3' end.

6. The oligonucleotide of claim 1, wherein the oligonucleotide is internally modified at an internucleoside linkage.

7. The oligonucleotide of claim 6, wherein the modified internucleoside linkage is a phosphorothioate linkage, a methylphosphonate linkage, or a phosphoroamidate linkage.

8. A composition comprising the oligonucleotide of claim 1 and ethambutol.

9. A composition comprising ethambutol and an oligonucleotide that hybridizes under physiological conditions to an aspartokinase gene, an aspartate semialdehyde dehydrogenase gene, or an aspartokinase-aspartate semialdehyde dehydrogenase operon of a Mycobacterium.

10. An oligonucleotide covalently coupled to a ligand that binds to a receptor on a *Mycobacterium smegmatis*; wherein the oligonucleotide hybridizes under physiological conditions to an aspartokinase gene, an aspartate semialdehyde dehydrogenase gene, or an aspartokinase-aspartate semialdehyde dehydrogenase operon of the *Mycobacterium smegmatis*; and wherein the ligand is D-cycloserine, D-glucosamine or biotin.

11. The oligonucleotide of claim 10, wherein the oligonucleotide is an oligodeoxynucleotide or an oligoribonucleotide.

12. The oligonucleotide of claim 10, wherein the oligonucleotide is a modified oligonucleotide.

13. The oligonucleotide of claim 10, wherein the oligonucleotide is covalently modified at the 5' end, the 3' end, or the 5' end and the 3' end.

14. The oligonucleotide of claim 10, wherein the oligonucleotide is internally modified at an internucleoside linkage.

15. The oligonucleotide of claim 14, wherein the modified internucleoside linkage is a phosphorothioate linkage, a methylphosphonate linkage, or a phosphoroamidate linkage.

16. The oligonucleotide of claim 10, wherein the oligonucleotide is complementary to nucleotide sequence 1533–1553, 1527–1553, or 1518–1553 of the *Mycobacterium smegmatis* ask-asd operon.

17. A composition comprising the oligonucleotide of claim 10 and ethambutol.

18. A composition comprising ethambutol and an oligonucleotide that hybridizes under physiological conditions to an aspartokinase gene, an aspartate semialdehyde dehydrogenase gene, or an aspartokinase-aspartate semialdehyde dehydrogenase operon of a *Mycobacterium smegmatis*.

19. An oligonucleotide covalently coupled to a ligand that binds to a receptor on a *Mycobacterium tuberculosis*; wherein the oligonucleotide hybridizes under physiological conditions to an aspartokinase gene, an aspartate semialdehyde dehydrogenase gene, or an aspartokinase-aspartate semialdehyde dehydrogenase operon of the *Mycobacterium tuberculosis*; and wherein the ligand is D-cycloserine, D-glucosamine or biotin.

20. The oligonucleotide of claim 19, wherein the oligonucleotide is an oligodeoxynucleotide or an oligoribonucleotide.

21. The oligonucleotide of claim 19, wherein the oligonucleotide is a modified oligonucleotide.

22. The oligonucleotide of claim 19, wherein the oligonucleotide is covalently modified at the 5' end, the 3' end, or the 5' end and the 3' end.

23. The oligonucleotide of claim 19, wherein the oligonucleotide is internally modified at an internucleoside linkage.

24. The oligonucleotide of claim 23, wherein the modified internucleoside linkage is a phosphorothioate linkage, a methylphosphonate linkage, or a phosphoroamidate linkage.

25. A composition comprising the oligonucleotide of claim 19 and ethambutol.

26. A composition comprising ethambutol and an oligonucleotide that hybridizes under physiological conditions to an aspartokinase gene, an aspartate semialdehyde dehydrogenase gene, or an aspartokinase-aspartate semialdehyde dehydrogenase operon of a *Mycobacterium tuberculosis*.

* * * * *